United States Patent [19]

Shields

[11] Patent Number: 6,107,529
[45] Date of Patent: *Aug. 22, 2000

[54] PURIFICATION OF 1,1,1,2-TETRAFLUOROETHANE

[75] Inventor: Charles John Shields, Stockton Heath, United Kingdom

[73] Assignee: Imperial Chemical Industries PLC, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/972,000

[22] Filed: Nov. 19, 1997

Related U.S. Application Data

[63] Continuation of application No. 08/356,338, filed as application No. PCT/GB93/01412, Jul. 6, 1993, abandoned.

[30] Foreign Application Priority Data

Jul. 8, 1992 [GB] United Kingdom .................... 9214449

[51] Int. Cl.$^7$ ..................................................... C07C 17/38
[52] U.S. Cl. ............................................................. 570/179
[58] Field of Search ................................................ 570/179

[56] References Cited

U.S. PATENT DOCUMENTS

| 4,906,706 | 3/1990 | Yates . | |
| 5,087,778 | 2/1992 | Yates | 570/179 |
| 5,160,499 | 11/1992 | Edwards | 570/179 |

FOREIGN PATENT DOCUMENTS

| 3072437 | 3/1991 | Japan | 570/179 |
| WO 91/15445 | 10/1991 | WIPO . | |

OTHER PUBLICATIONS

Chemical Abstracts, vol. 115, No. 17, Oct. 28, 1991, Columbus, Ohio, US; Abstract No. 182607b.

*Primary Examiner*—Alan Siegel
*Attorney, Agent, or Firm*—Cook, Alex, McFarron, Manzo, Cummings & Mehler, Ltd.

[57] ABSTRACT

A process for the removal of 1,1,2,2-tetrafluoroethane from 1,1,1,2-tetrafluoroethane which comprises contacting 1,1,1,2-tetrafluoroethane containing 1,1,2,2-tetrafluoroethane with a zeolite having a mean pore size in the range of 3.8 Å an 4.8 Å. The zeolite is preferably calcium chabazite.

11 Claims, No Drawings

PURIFICATION OF 1,1,1,2-TETRAFLUOROETHANE

This is a continuation, of application Ser. No. 08/356,338 filed on Dec. 22, 1994 now abandoned, which is a 371 of PCT/GB93/01412, filed Jul. 6, 1993.

This invention relates to a process for the purification of 1,1,1,2-tetrafluoroethane and in particular to a process for the removal of 1,1,2,2-tetrafluoroethane from 1,1,1,2-tetrafluoroethane.

In recent years chlorofluorocarbons (CFCs), which are used on a large scale around the world, have been perceived as having an adverse effect on the ozone layer and/or as contributing to global warming. CFCs are used, for example, as refrigerants, as foam blowing agents, as cleaning solvents and as propellants for aerosol sprays in which the variety of applications is virtually unlimited. Consequently, attempts have been made to find suitable replacements which will perform satisfactorily in the many applications in which CFCs are used but which will not have the aforementioned damaging effect on the ozone layer. The search for suitable replacements has in general centred on fluorocarbons which do not contain chlorine. The hydrofluorocarbon, 1,1,1,2-tetrafluoroethane, also known as HFA 134a, has been of particular interest as one such replacement, in particular as a replacement for dichlorodifluoromethane (CFC 12) in refrigeration applications.

HFA 134a may be produced in a variety of ways, amongst which may be mentioned hydrogenation of a chlorofluorocarbon, and fluorination of an alkene or a hydrochlorofluorocarbon with hydrogen fluoride or an alkali metal fluoride; a catalyst such as chromia, halogenated chromia or chromium oxyhalide may be employed to facilitate the reaction.

However, a characteristic of known processes for the production of HFA 134a is that many by-products tend to be produced. Some of the by-products are easy to separate by distillation. However a by-product which it is desirable to remove, or at least reduce to low levels, for example below 50 ppm, is 1,1,2,2-tetrafluoroethane (HFA 134). HFA-134 has a boiling point close to that of HFA 134a, making them difficult to separate by distillation.

It has already been proposed to use certain types of molecular sieve for the removal of HCFC 1122 from HFA 134a. Thus, for example in U.S. Pat. No. 4,906,790 there is disclosed a process for the removal of HCFC 1122 from HFA 134a in which an HFA 134a stream is passed over a molecular sieve which has a pore size of 3.8 to 4.8 Angstroms; the sieve may be carbon or a zeolite such as zeolite 5A or calcium chabazite. It is noted that in this U.S. patent the zeolites described have little or no capacity for other impurities, including other hydrofluoroalkanes, making the adsorption of HCFC 1122 very selective.

However we have now found that HFA 134 may also be removed from HFA 134a by contact with certain zeolites despite both the similarity of the molecules of HFA 134 and HFA 134a and the prior belief that hydrofluoroalkanes were not adsorbed by these zeolites.

According to the present invention there is provided a process for the removal of 1,1,2,2-tetrafluoroethane from 1,1,1,2-tetrafluoroethane which comprises contacting 1,1,1,2-tetrafluoroethane containing 1,1,2,2-tetrafluoroethane with a zeolite having a mean pore size in the range of 3.8 Å and 4.8 Å. The zeolite preferably has a mean pore size in the range from about 3.8Å to about 4.5Å, especially from about 3.8Å to about 4.2 Å.

Particularly useful zeolites include 5A synthetic zeolites and the naturally derived chabazite zeolites, for example calcium chabazite, commercially available as AW-500. AW-500 is particularly preferred.

Prior to use of the zeolite in the process of the invention, the zeolite should be dried and this may be achieved, for example, by heating the zeolite to a temperature of between about 200° C. and about 400° C. in a nitrogen atmosphere at atmospheric pressure or at a lower temperature under sub-atmospheric pressure.

In the process of the invention, HFA 134a containing HFA 134 and optionally other halocarbon impurities, for example hydrofluorocarbon and hydrochlorofluorocarbon impurities, may be contacted with the zeolite by passing a stream of HFA 134a in the liquid or vapour phase over a bed of zeolite particles. The bed may be a fixed bed. Alternatively various other techniques, known in the art, may be used for contacting an HFA 134a stream with the zeolite adsorbent such as, for example, contacting the stream with a fluidised or moving bed of adsorbent zeolite particles. Selection of the particle size and bed shape may be varied within a broad range and may be determined according to known principles. The zeolite particle size depends at least to some extent upon whether vapour phase or liquid phase contacting is employed and upon the scale of the process, but overall the particle size will usually be in the range from about 1 micrometer to about 5 centimetres, and preferably in the range from about 500 micrometers to about 1 centimetre.

The hourly space velocity of the HFA 134a stream over the zeolite may be varied within a wide range. Generally, HFA 134a vapour may be passed over the zeolite with a gas hourly space velocity of 10 to 3600 hr$^{-1}$, although the gas hourly space velocity may be much greater than this if desired, particularly at lower temperatures. The corresponding liquid hourly space velocity for liquid phase operation is 1 to 30 hr$^{-1}$.

The temperature at which the purification process is carried out will typically be in the range from about −30° C. to about 100° C. The pressure at which the process is carried out may be dependent to some extent upon whether liquid or vapour phase contacting is desired but will usually be in the range from about 1.0 to about 40 bar.

Typically, the HFA 134a as produced by conventional processes, and treated by the process of the invention will contain from about 100 to about 10000 ppm HFA 134 although it may contain a substantially higher concentration of HFA 134. Use of the zeolites of the invention allows the removal of HFA 134 from HFA 134a to a very low level, generally below 50 ppm, and even below 20 ppm, depending to some extent on the initial HFA 134 content of the HFA 134a.

HFA 134a as produced by known processes may contain further contaminants in addition to HFA 134. These contaminants include, for example, single-carbon and two-carbon species containing hydrogen, chlorine and fluorine, as well as unreacted hydrogen fluoride and by-product hydrogen chloride (which is a major by-product from most known HFA 134a production processes). The hydrogen fluoride and hydrogen chloride can be removed by known techniques; preferably, since hydrogen fluoride and hydrogen chloride may attack the zeolites used in the process of the invention, the removal of hydrogen fluoride and hydrogen chloride is carried out prior to contacting the HFA 134a stream with the zeolite. Other contaminants are typically present in only very small amounts and many may be removed by distillation.

The adsorbent zeolite bed will require regeneration or reactivation when its capacity for adsorbing HFA 134 has been filled. Regeneration may be, for example, by heating the bed in a gas stream, usually nitrogen or air, to desorb the HFA 134. After the bed has been heated and HFA 134 fully removed from it, it may be cooled and re-introduced into service. The optimum conditions required to regenerate the adsorbent will be determined by the particular adsorbent used and the available utilities and are readily determined by simple routine experiment. Typically, heating the bed of adsorbent to between about 70° C. and about 400° C. within a stream of nitrogen gas or air provides satisfactory regeneration.

The invention is illustrated by the following example.

A 100 ml aerosol container was charged with 4.03 g of AW 500 zeolite and 49 g of liquid HFA 134a containing 350 ppm of HFA 134. The aerosol was sealed and allowed to stand for 24 hours at ambient temperature after which time the liquid was analysed by gas chromatography. The level of HFA 134 in the liquid had been reduced to 17 ppm.

What is claimed is:

1. A process for the removal of 1,1,2,2tetrafluoroethane from 1,1,1,2-tetrafluoroethane obtained by the hydrogenation of a chlorofluorocarbon or hydrochlorofluorocarbon which process comprises contacting 1,1,1,2-tetrafluoroethane containing 1,1,2,2-tetrafluoroethane with a zeolite having a mean pore size in the range of 3.8 to 4.8 Angstroms and heating the zeolite, when the capacity of the zeolite for adsorbing 1,1,2,2-tetrafluoroethane has been filled, in a gas stream, to desorb the 1,1,2,2-tetrafluoroethane.

2. A process for the removal of 1,1,2,2-tetrafluoroethane from 1,1,1,2-tetrafluoroethane obtained by the hydrofluorination of an alkene or a hydrochlorofluorocarbon which process comprises contacting 1,1,1,2-tetrafluoroethane containing 1,1,2,2-tetrafluoroethane with a zeolite having a mean pore size in the range of 3.8 to 4.8 Angstroms and heating the zeolite, when the capacity of the zeolite for adsorbing 1,1,2,2-tetrafluoroethane has been filled, in a gas stream, to desorb the 1,1,2,2-tetrafluoroethane.

3. A process for the removal of 1,1,2,2-tetrafluoroethane from 1,1,1,2-tetrafluoroethane which comprises contacting a stream comprising 1,1,1,2-tetrafluoroethane and, at a level of 100 to 10,000 ppm, 1,1,2,2-tetrafluoroethane with a zeolite having a mean pore size in the range 3.8 to 4.8 Angstroms, recovering a stream comprising 1,1,1,2-tetrafluoroethane and, at a level of less than 50 ppm, 1,1,2,2-tetrafluoroethane and heating the zeolite, when the capacity of the zeolite for adsorbing 1,1,2,2-tetrafluoroethane has been filled, in a gas stream, to desorb the 1,1,2,2-tetrafluoroethane.

4. A process as claimed in claims 1, 2 or 3 in which the zeolite has a mean pore size in the range from about 3.8 to about 4.2 Angstroms.

5. A process as claimed in claims 1, 2, or 3 in which the zeolite is a 5A synthetic zeolite or a naturally derived chabazite zeolite.

6. A process as claimed in claims 1, 2, or 3 which comprises passing a stream of 1,1,1,2-tetrafluoroethane containing 1,1,2,2-tetrafluoroethane in the liquid or vapor phase over a bed of zeolite particles having a mean particle size in the range from about 1 micrometer to about 5 centimeters.

7. A process as claimed in claims 1, 2, or 3 in which 1,1,1,2-tetrafluoroethane vapor is passed over the zeolite with a gas hourly space velocity of 10 to 3600 hr$^{-1}$.

8. A process as claimed in claims 1, 2, or 3 wherein the 1,1,1,2-tetrafluoroethane is in the liquid phase and the liquid hourly space velocity is 1 to 30 hr$^{-1}$.

9. A process as claimed in claims 1, 2 or 3 in which the temperature is from about −30° C. to about 100° C.

10. A process as claimed in claims 1 or 2 in which the 1,1,1,2-tetrafluoroethane which is contacted with the zeolite contains from about 100 to about 10000 ppm 1,1,2,2-tetrafluoroethane and the 1,1,1,2-tetrafluoroethane which is recovered from the process contains less than about 50 ppm 1,1,2,2-tetrafluoroethane.

11. A process as claimed in claims 1, 2, or 3 which further comprises heating the zeolite after use in a gas stream whereby to desorb the 1,1,2,2-tetrafluoroethane.

* * * * *